United States Patent [19]

Sawhill et al.

[11] 3,993,649

[45] Nov. 23, 1976

[54] PROCESS FOR PREPARING HALOISOCYANURIC ACIDS

[75] Inventors: Duane L. Sawhill, Plainfield, Ill.; Henry W. Schiessl, Northford, Conn.

[73] Assignee: Olin Corporation, New Haven, Conn.

[22] Filed: June 30, 1975

[21] Appl. No.: 591,576

[52] U.S. Cl............................................. 260/248 C
[51] Int. Cl.²....................................... C07D 251/36
[58] Field of Search ................................ 260/248 C

[56] References Cited

UNITED STATES PATENTS 3,712,891  1/1973  Berkowitz............................ 260/248

*Primary Examiner*—John M. Ford
*Attorney, Agent, or Firm*—James B. Haglind; Donald F. Clements; Thomas P. O'Day

[57] ABSTRACT

Haloisocyanuric acids are prepared in a process in which solid cyanuric acid is reacted with a dihalogen monoxide gas, such as dichlorine monoxide or dibromine monoxide.

10 Claims, No Drawings

PROCESS FOR PREPARING HALOISOCYANURIC ACIDS

This invention relates to a process for producing polyhaloisocyanuric acids by the halogenation of cyanuric acid. Polyhaloisocyanurates are well known commerical products used in bleaching and sanitizing applications.

It is known to prepare polyhaloisocyanuric acids, for example, di- or tri- chloroisocyanuric acids by the reaction of cyanuric acid with chlorine or hypochlorous acid in an aqueous medium. The polychloroisocyanuric acids produced are only incompletely recovered as a portion remains dissolved in the aqueous medium. This soluble portion is recovered with difficulty or if not recovered, the waste solution must be properly treated. Either recovery of the haloisocyanuric acid or disposal of the waste solutions involve considerable expense. In addition, when chlorine is employed as a reagent, it is necessary to employ a sufficient amount of an alkali to neutralize hydrochloric acid produced during the reaction. Further, the polychloroisocyanuric acid is less stable in the presence of the alkali metal salt formed and greater amounts of polychloroisocyanuric acid remain in the aqueous medium.

The preparation of polyhaloisocyanuric acids by the reaction of cyanuric acid with dihalogen monoxides in an organic solvent medium is also known. This process, as described in U.S. Pat. No. 3,352,860, Nov. 14, 1967, issued to Hass et al, requires the separation of the polyhaloisocyanuric acid produced from the solvent and subsequent removal of organic impurities from the product.

In addition, in both of the above methods of preparation, the polychloroisocyanuric acid is obtained as a wet product which must be dried to be sold commercially or suitably used in many applications.

There is need therefore of a process for the production of polyhaloisocyanuric acids which does not require use of a liquid solvent medium and a separate drying step.

An object of the present invention is a novel process for producing polyhaloisocyanuric acids in the absence of solvents.

Another object of the present invention is a process for producing polyhaloisocyanuric acids which provides complete recovery of the products.

A further object of the present invention is a process in which a polyhaloisocyanuric acid is obtained directly as a dry product.

These and other objects of the invention will be apparent from the following detailed description of the invention.

Briefly, the process of the present invention for producing polyhaloisocyanuric acids comprises reacting a dihalogen monoxide gas with solid cyanuric acid and recovering the polyhaloisocyanuric acid produced.

Suitable dihalogen monoxides which can be used in the novel process of the present invention include dichlorine monoxide and dibromine monoxide. These are prepared by processes well known in the prior art, for example, by the reaction of the halogen gas with mercuric oxide according to the equation:

$$2X_2 + 2HgO \rightarrow X_2O + HgX_2 \cdot HgO \qquad (1)$$

wherein X is chlorine or bromine.

Another suitable method of preparation for dichlorine monoxide is the chlorination of sodium carbonate or sodium bicarbonate illustrated by the following equations:

$$2Cl_2 + 2Na_2CO_3 + H_2O \rightarrow Cl_2O + 2NaHCO_3 + 2NaCl \qquad (2)$$

$$2Cl_2 + 2NaHCO_3 \rightarrow Cl_2O + 2CO_2 + H_2O + 2NaCl \qquad (3)$$

A detailed procedure for each of these methods of preparation for dichlorine monoxide is given in the publication Inorganic Synthesis, 5, 156-160, (N.Y. McGraw-Hill, 1957). The preparation of dibromine monoxide is described in "Bromine and Its Compounds" edited by E. Jolles, (N.Y., Academic Press, 1966) pages 148–49.

Cyanuric acid, the second reactant, is a commercially available product which is used in this invention in the solid form. Solid hydrates of cyanuric acid or the anhydrous form may be suitably used. Ground or unground solid cyanuric acid may be employed. However, it is preferred to use ground cyanuric acid having a particle size distribution in the range of from about 2 to about 300 microns, and preferably from about 10 to about 150 microns.

The reaction of the dihalogen monoxide gas with cyanuric acid to produce, for example, trihaloisocyanuric acid proceeds according to the following equation:

$$2H_3C_3N_3O_3 + 3X_2O \rightarrow 2X_3C_3N_3O_3 + 3H_2O \qquad (4)$$

wherein X is chlorine or bromine.

Where the dihaloisocyanuric acid is the desired product, the equation illustrating the reaction is:

$$H_3C_3N_3O_3 + X_2O \rightarrow HX_2C_3N_3O_3 + H_2O \qquad (5)$$

The process of the present invention is conducted in a reactor by passing the dihalogen monoxide gas over or through solid cyanuric acid. The cyanuric acid is preferably retained on a foraminous support.

A molar ratio of dihalogen monoxide gas to cyanuric acid of at least about 1:1 is the stoichiometric proportion required to form a polyhaloisocyanuric acid in accordance with the process of this invention. As shown in Equation (5), the product is a dihaloisocyanuric acid when the molar ratio is 1:1 and, as shown in Equation (4), the product is a trihaloisocyanuric acid when the molar ratio is 1.5:1. The proportion of dihalogen monoxide gas fed to the reactor may range from about 1:1 to about 10:1, and preferably an excess of dihalogen monoxide gas is employed. When a dihaloisocyanuric acid product is desired, the molar ratio preferably ranges from about 1:1 to about 1.3:1. When a trihaloisocyanuric acid product is desired, the molar ratio preferably ranges from about 1.5:1 to about 5:1. One skilled in the art will recognize that a molar ratio of less than 1:1 will produce some dihaloisocyanuric acid and a molar ratio of less than about 1:5:1 will produce some trihaloisocyanuric acid.

During the reaction between the dihalogen monoxide and cyanuric acid as shown in equations 4 and 5, water is produced as a by-product.

The reaction conditions are selected to prevent substantial amounts of the water produced from condensing. The reaction takes place at any suitable temperature above that of the dew point and up to about 200° C.

For example, when the reaction is carried out at atmospheric pressure, a reaction temperature of about 100° C. is maintained to vaporize the water produced.

When conducting the reaction at pressures below or above atmospheric, the reaction temperature can be reduced or increased accordingly. In a preferred embodiment, a gas inert to the reaction is supplied to the reaction vessel to remove the water as it is formed and prevent condensation thereof. Suitable gases include air, nitrogen, carbon dioxide, or chlorine, with air or nitrogen being preferred. The inert gas may be supplied either as a mixture with the dihalogen monoxide or separately. The temperature and flow rates for the inert gas are selected to suitably remove the by-product water produced. For example, in the production of trichloroisocyanuric acid at a reaction temperature of 30° C., about 1 cubic meter of inert gas is supplied for each mole of trichloroisocyanuric acid produced.

Where the process is conducted in a fluidized bed reactor, the inert gas can be used advantageously to fluidize the cyanuric acid. The principles and practice of employing fluidized bed reactors are well known as described, for example, in the Chemical Engineers Handbook edited by R. H. Perry and C. H. Chilton, 5th edition, New York, McGraw-Hill, 1973, Section 20, pages 64–74.

Where a fluidized bed reactor is not employed, it may be desirable to agitate the cyanuric acid by mechanical means or to employ a rotating reactor having means such as flights to cascade the cyanuric acid.

Haloisocyanurates produced by the process of the present invention are recovered as dry or slightly moist products which can be used directly with no further processing required, except, if desired, additional drying.

An additional advantage is that the potentially hazardous nitrogen trichloride, which is often produced in processes of the prior art, was not detected during the reaction between cyanuric acid and dichlorine monoxide.

The process of the present invention is further illustrated by the following examples. All percentages are by weight unless otherwise specified.

EXAMPLE 1

Cyanuric acid (10 parts) was micropulverized to provide particles having a size range of from about 50 microns to about 75 microns. The cyanuric acid was added to a reaction vessel equipped with a magnetic stirrer. Dichlorine monoxide (25 mls. per min.) was generated by feeding dry chlorine gas to a reactor containing a mixture of dried yellow mercuric oxide and glass beads. Nitrogen gas (100 mls. per min.) was added to the dichlorine monoxide and the gaseous mixture fed to the reaction vessel. The reaction was conducted for about four hours at ambient temperature. A dry, free-flowing product identified by infrared spectrum analysis, as trichloroisocyanuric acid was obtained, having an available chlorine content of 87.3% (theoretical 91.67%).

EXAMPLE 2

To a horizontal fixed bed reactor containing 25 parts of unground cyanuric acid was charged 2.5 liters per hour of dichlorine monoxide, generated as in Example 1. Dry air was also added to the reactor at a flow rate of 7.5 liters per hour. After about 1/2 hour the reaction was stopped, the cyanuric acid particles agitated and the reaction resumed for an additional 1/2 hour. A dry chloroisocyanuric acid product having an available chlorine content of 18 percent was produced.

What is claimed is:

1. A process for the production of polyhaloisocyanuric acids comprising reacting a dihalogen monoxide gas with solid cyanuric acid in a reaction mixture and recovering said haloisocyanuric acid produced.

2. The process of claim 1 wherein said dihalogen monoxide is selected from the group consisting of dichlorine monoxide, dibromine monoxide or mixtures thereof.

3. The process of claim 2 wherein said polyhaloisocyanuric acid is selected from the group consisting of a chloroisocyanuric acid, a bromoisocyanuric acid, and mixtures thereof, and the molar ratio of said dihalogen monoxide to said cyanuric acid is from at least about 1:1 to about 10:1.

4. The process of claim 3 wherein said reaction is conducted at a temperature above that of the dew point and up to about 200° C.

5. The process of claim 4 wherein said dihalogen monoxide is dichlorine monoxide, and said polyhaloisocyanuric acid is a chloroisocyanuric acid.

6. The process of claim 5 wherein said molar ratio of said dichlorine monoxide to said cyanuric acid is from about 1:1 to about 1.3:1 and said chloroisocyanuric acid is dichloroisocyanuric acid.

7. The process of claim 5 wherein said molar ratio of said dichlorine monoxide to said cyanuric acid is from about 1.5:1 to about 5:1, and said chloroisocyanuric acid is trichloroisocyanuric acid.

8. The process of claim 5 wherein a gas selected from the group consisting of air, nitrogen, and carbon dioxide is added to said reaction mixture.

9. The process of claim 8 wherein said cyanuric acid has a particle size of from about 2 to about 300 microns.

10. The process of claim 9 wherein the mole ratio of dichlorine monoxide to cyanuric acid is from about 1.5:1 to about 5:1 and said chloroisocyanuric acid is trichloroisocyanuric acid.

* * * * *